United States Patent [19]

Gerry et al.

[11] Patent Number: 5,409,478

[45] Date of Patent: Apr. 25, 1995

[54] HANDLE FOR MANIPULATING LAPAROSCOPIC TOOL

[75] Inventors: Stephen W. Gerry, Bethel; David T. Green, Westport; Henry Bolanos, East Norwalk, all of Conn.

[73] Assignee: United States Surgical Corporation, Norwalk, Conn.

[21] Appl. No.: 39,520

[22] Filed: Mar. 29, 1993

Related U.S. Application Data

[63] Continuation of Ser. No. 770,543, Oct. 3, 1991.

[51] Int. Cl.⁶ .............................................. A61B 17/00
[52] U.S. Cl. ......................................... 606/1; 606/108
[58] Field of Search ................................ 128/95, 772; 604/208–211; 606/1, 107, 108, 113, 127, 138–148, 205–211

[56] References Cited

U.S. PATENT DOCUMENTS

| | | | |
|---|---|---|---|
| 1,310,982 | 7/1919 | Davis | 606/113 |
| 1,452,373 | 4/1923 | Gomez . | |
| 1,606,497 | 11/1926 | Berger | 606/113 |
| 1,659,112 | 2/1928 | Littlejohn . | |
| 2,363,334 | 11/1944 | Jones . | |
| 2,898,915 | 8/1959 | Kammer . | |
| 2,898,916 | 8/1959 | Kammer . | |
| 3,452,740 | 7/1969 | Muller | 606/108 |
| 3,517,668 | 6/1970 | Brickson | 604/209 |
| 3,807,406 | 4/1974 | Rafferty et al. . | |
| 3,913,584 | 10/1975 | Walchle et al. | 606/108 |
| 3,964,468 | 6/1976 | Schulz . | |
| 4,049,002 | 9/1977 | Kletschka et al. . | |
| 4,178,810 | 12/1979 | Takahashi | 606/1 |
| 4,258,716 | 3/1981 | Sutherland . | |
| 4,406,654 | 9/1983 | Bristow | 604/209 |
| 4,411,653 | 10/1983 | Razi | 606/108 |
| 4,428,374 | 1/1984 | Auburn . | |
| 4,433,687 | 2/1984 | Burke et al. . | |
| 4,480,640 | 11/1984 | Becht . | |
| 4,572,185 | 2/1986 | Rich . | |
| 4,576,166 | 3/1986 | Montgomery et al. . | |
| 4,598,711 | 11/1986 | Deniega . | |
| 4,611,595 | 9/1986 | Klieman et al. . | |
| 4,614,187 | 9/1986 | Mulhollan et al. . | |
| 4,643,190 | 2/1987 | Heimberger . | |
| 4,662,371 | 5/1987 | Whipple et al. . | |
| 4,669,647 | 6/1987 | Storace . | |

(List continued on next page.)

FOREIGN PATENT DOCUMENTS

| | | | |
|---|---|---|---|
| 0027704 | 4/1981 | European Pat. Off. | 606/113 |
| 0240722 | 10/1987 | European Pat. Off. . | |
| 0392547 | 10/1990 | European Pat. Off. . | |
| 0392548 | 10/1990 | European Pat. Off. . | |
| 2542188 | 9/1984 | France . | |
| 220437 | 4/1961 | Germany . | |
| 3301803 | 6/1984 | Germany | 606/138 |
| 3709706 | 10/1987 | Germany . | |
| 1561964 | 5/1990 | U.S.S.R. | 060/148 |

OTHER PUBLICATIONS

Padgett Instruments Bulletin, Jun. 6, 1976.
Solos Endoscopy Brochure.

*Primary Examiner*—Stephen C. Pellegrino
*Assistant Examiner*—Glenn Dawson

[57] ABSTRACT

A handle for a laparoscopic instrument is provided for manipulating a distal laparoscopic tool. The handle includes a casing, a pivot handle pivotally attached to the casing, and an actuating shaft mechanism extending outward from the casing. Attached at the distal end of the actuating shaft opposite the casing is the laparoscopic surgical tool. The actuating shaft mechanism is longitudinally movable in a first direction by a pivotal movement of the pivot handle for manipulating the laparoscopic tool. A detent carried by the casing allows movement of the shaft longitudinally in the first direction while restraining longitudinal movement of the shaft in a second opposite direction. A thumb wheel attached to the actuating shaft mechanism allows the actuating shaft mechanism to be rotated for further manipulating the laparoscopic tool.

56 Claims, 3 Drawing Sheets

U.S. PATENT DOCUMENTS

| | | | |
|---|---|---|---|
| 4,710,172 | 12/1987 | Jacklich et al. | 604/209 |
| 4,710,178 | 12/1987 | Leonard et al. | 604/209 |
| 4,712,545 | 12/1987 | Honkanen . | |
| 4,785,810 | 11/1988 | Baccala et al. . | |
| 4,820,287 | 4/1989 | Leonard | 604/209 |
| 4,896,661 | 1/1990 | Bogert et al. . | |
| 4,898,157 | 2/1990 | Messroghli et al. . | |
| 4,909,789 | 3/1990 | Taguchi et al. . | |
| 4,921,423 | 5/1990 | Kesling | 606/140 |
| 4,935,027 | 6/1990 | Yoon . | |
| 4,950,273 | 8/1990 | Briggs | 606/113 |
| 4,976,716 | 12/1990 | Cumming . | |
| 5,009,661 | 4/1991 | Michelson . | |
| 5,049,152 | 9/1991 | Simon et al. | 606/139 |
| 5,084,057 | 1/1992 | Green et al. | 606/142 |
| 5,100,420 | 3/1992 | Green et al. . | |

HANDLE FOR MANIPULATING LAPAROSCOPIC TOOL

This is a continuation of copending application Ser. No. 07/770,543, filed on Oct. 3, 1991.

BACKGROUND OF THE INVENTION

1. Field of the Invention

The present invention relates to the field of laparoscopic or endoscopic surgery, and more particularly to a handle mechanism for manipulating a distal laparoscopic surgical tool inserted through a small incision in the body and positioned within the body adjacent an organ which is to be excised or repaired, allowing surgical procedures to be performed thereon.

2. Discussion Of The Prior Art

A surgeon, when performing an operation on a patient, is often obstructed in his efforts to excise diseased or damaged tissues or organs by surrounding tissues, fatty deposits, arteries, or other organs. It has generally been the case, when performing gastro intestinal surgery, i.e. surgery within the abdominal cavity, to make a large cut in the abdomen wall to produce a suitable opening to allow access to the interior organs. This cut was generally large enough to allow the use of human hands, either those of the surgeons or those of a member of the surgical team, as a retractor. Surgical personnel would thus insert their hands through the incision into the abdominal cavity to push and hold organs and other obstructing components away from the surgical objective.

Recently, at least in part as a result of the evolution in electronic video technology, a surgical procedure known as laparoscopic surgery has undergone a marked increase in popularity. The laparoscope consists of a long thin rigid tube, and residing at one end of the tube is a viewing lens, while at the opposite end is a camera hook up and an eye piece. A small incision in the area of the surgical objective is made and the laparoscope is partially inserted into this incision, viewing lens first. High definition video cameras and monitors are then attached to the camera hook up connector on the part of the laparoscope which remains positioned exteriorly of the body. In this manner, a surgical team can get a clear picture of the affected internal area without resorting to radical, disfiguring surgical incisions to physically open the patient. Other small incisions may then be made through the surface of the skin in the vicinity of the surgical objective. Through these incisions, miniaturized surgical instruments such as scissors, forceps, clamps and scalpels may be inserted to perform various surgical procedures. The entire interiorly performed surgical procedure is monitored from the exterior through the high definition television monitor. In this manner radical incisions and scarring are avoided while undertaking surgical repair or removal of damaged or diseased organs. Another benefit of laparoscopic surgery is the significantly reduced recovery time, when compared to standard surgical procedures, due to the minuscule size of the scalpel incisions and avoidance of the massive internal traumatization known in standard surgical procedures. Accompanying the reduced recovery time are, of course, greatly reduced costs.

Therefore, there is a need to provide a device which may be partially inserted through a tiny surgical incision in the abdominal wall, which may be used during laparoscopic surgery within the abdominal cavity, and which is useful to manipulate an endoscopic surgical tool held distally at the end of the device within the abdominal cavity adjacent that organ which is being excised or repaired.

Several implements are known which are useful to perform certain surgical procedures. For example, U.S. Pat. No. 2,898,915 discloses an implement for particularly tying off open blood vessels astringently. When the operating handle is suitably depressed, a catch is released so that the main slide member under the action of a spring will slide quickly forward into the casing, allowing the tying head of the implement to move over the forceps, with its front surface even extending slightly beyond. For a further device for ligaturing blood vessels see U.S. Pat. No. 2,898,916 wherein by pressing the operating lever against the casing of the device, a second lever connected to the operating lever is moved laterally, and presses with a closing effect against a pivotally connected clamping arm so that it closes against a stationary clamping arm, clamping the blood vessel closed so that it may be ligatured.

However, these types of implements are not useful for imparting longitudinal and rotative movements to various endoscopic tools to manipulate their action during endoscopic surgery.

SUMMARY OF THE INVENTION

The present invention provides a novel handle for an endoscopic or laparoscopic tool which may be inserted through a tiny surgical incision in the abdominal wall, which may be used during laparoscopic surgery within the abdominal cavity, and which is useful to manipulate the endoscopic surgical tool held distally at the end of the device within the abdominal cavity adjacent that organ which is being excised or repaired. Accordingly, the device according to the present invention may impart longitudinal and rotative movements to various endoscopic tools to manipulate their action during endoscopic surgery.

The device according to the present invention is a novel handle for a laparoscopic or endoscopic instrument which may, by imparting longitudinal and rotative motion selectively to a pair of concentric longitudinal shafts that extend outwardly from the handle, manipulate a distal laparoscopic surgical tool held at the opposite end of the shafts. In order to impart longitudinal motion to manipulate the distal laparoscopic surgical tool, the handle is provided with an axially aligned, elongated casing and a pivotally connected elongated grip member extending generally axially along the casing. The grip member, together with the casing, provide a pair of operating handles movable toward and away from each other. When the grip member is squeezed laterally inward, longitudinal movement is imparted to the inner, actuating shaft of the paired shafts. To impart longitudinal motion in a first direction, the grip member pivots from a first position laterally inward to a second position contacting along the casing and generally co-axial with the shafts.

The casing, into which the concentric shafts axially extend, encloses the details of the present invention. A link member pivotally interconnects the grip member and a rack attached at the enclosed end of the actuating shaft and located within the casing. The actuating shaft is connected to the rack so that it moves longitudinally with the rack. As the grip member is squeezed inward towards its second position, the link translates the pivotal motion of the grip member to longitudinal motion to impart a longitudinal movement to the rack and actuating shaft in the first direction toward the rear end of the casing. The longitudinal movement of the actuating shaft in the first direction, imparted by squeezing the grip member laterally inward toward its second position, causes a manipulative longitudinal movement to be applied to the distal laparoscopic surgical tool to perform a specified surgical procedure. As may be appreciated, a longitudinal slot is provided in the casing through which the link member extends to allow the link to move longitudinally in the casing as the grip member is squeezed.

A detent enclosed within the casing allows the rack to slide therealong in the first direction so that the rack and attached actuating shaft may move longitudinally in the first direction. The detent engages with the rack to restrain longitudinal movement of the rack and attached actuating shaft in a second direction, opposite the first direction, toward the front end of the casing. The detent and the rack cooperate to allow for incremental "ratcheting action" which allows the laparoscopic surgical tool to be selectively incrementally manipulated by squeezing the grip member inward in suitable increments towards its second position. Thus, the tool may be advanced through a series of incremental positions as the grip member is moved incrementally to its second position.

A release mechanism allows the rack and attached actuating shaft to move longitudinally in the second direction. As may be further appreciated, the release mechanism also allows the grip member and link member to return to their first position. The release mechanism includes an elongated release member which extends longitudinally into the casing. The release member is longitudinally movable from a first locking position by finger action to a second position to release the detent from its engagement with the rack. Included with the release mechanism, is a catch located on the detent which when engaged by the release member, allows the release member to disengage the detent from the rack. The catch is engaged by the enclosed end of the release member when the release member is moved to its second position, and, when the release member is moved to its second position allows the release member to disengage the detent from the rack. In order to impart longitudinal motion to the actuating shaft and rack in the second direction when the release member is moved to its second position, a spring located between the casing and the rack acts on the rear end of the rack to longitudinally move the actuating shaft and rack in the second direction. The longitudinal movement of the actuating shaft in the second direction, imparted by moving the release button to its second position, causes a further manipulative longitudinal movement to be applied to the distal laparoscopic surgical tool to return the tool to its initial configuration.

A thumb wheel is engaged with the outer shaft, and, when rotated, causes the shafts to rotate about their longitudinal axis. The rotational movement of the actuating shaft, imparted by rotating or turning the thumb wheel, causes a manipulative rotational movement to be applied to the distal laparoscopic surgical tool to perform a further specified surgical procedure. Accordingly, the manipulative rotational movement may be applied to rotate the laparoscopic tool in an arc about the longitudinal axis of the concentric shafts. Consequently, the tool may not need to be repositioned in the body to access that bodily organ to be excised or repaired even though the tool may be initially deflected from its designated plane of operation. Instead, rotation of the thumb wheel may allow the tool to be repositioned within the desired operating plane. The rotational motion may be applied either clockwise or counter-clockwise to align the surgical tool within the operating plane and to return the tool to its initial position.

Thus, after a trocar is partially inserted in the body, the laparoscopic surgical tool attached at the distal end of the concentric shafts may be inserted through the cannula of the trocar and positioned adjacent the organ to be excised or repaired. With the aid of a laparoscope, the surgeon can manipulate the distal laparoscopic surgical tool by squeezing the grip member laterally, in suitable increments, inward toward the casing and alignment with the axis of the concentric shafts to selectively apply longitudinal motion to the laparoscopic surgical tool. Thus, the tool may be selectively manipulated to perform a specific surgical procedure. When the grip member is moved incrementally toward the casing, the detent and the rack cooperate to allow for the incremental "ratcheting action" which allows the laparoscopic surgical tool to be selectively incrementally manipulated.

Manipulation of the laparoscopic tool to position the surgical tool in the plane of operation may be performed by rotating the thumb wheel. As may be appreciated, this may allow better use of the laparoscopic surgical tool. Pressing inward on the push button end of the release member to disengage the detent from the rack, causes the laparoscopic surgical tool to return towards an initial configuration under spring influence.

BRIEF DESCRIPTION OF THE DRAWINGS

The foregoing features of the present invention will become more readily apparent and may be understood by referring to the following detailed description of a preferred embodiment of the handle according to the present invention, taken in conjunction with the accompanying drawings, in which.

DETAILED DESCRIPTION OF THE PREFERRED EMBODIMENT

Figure 1:
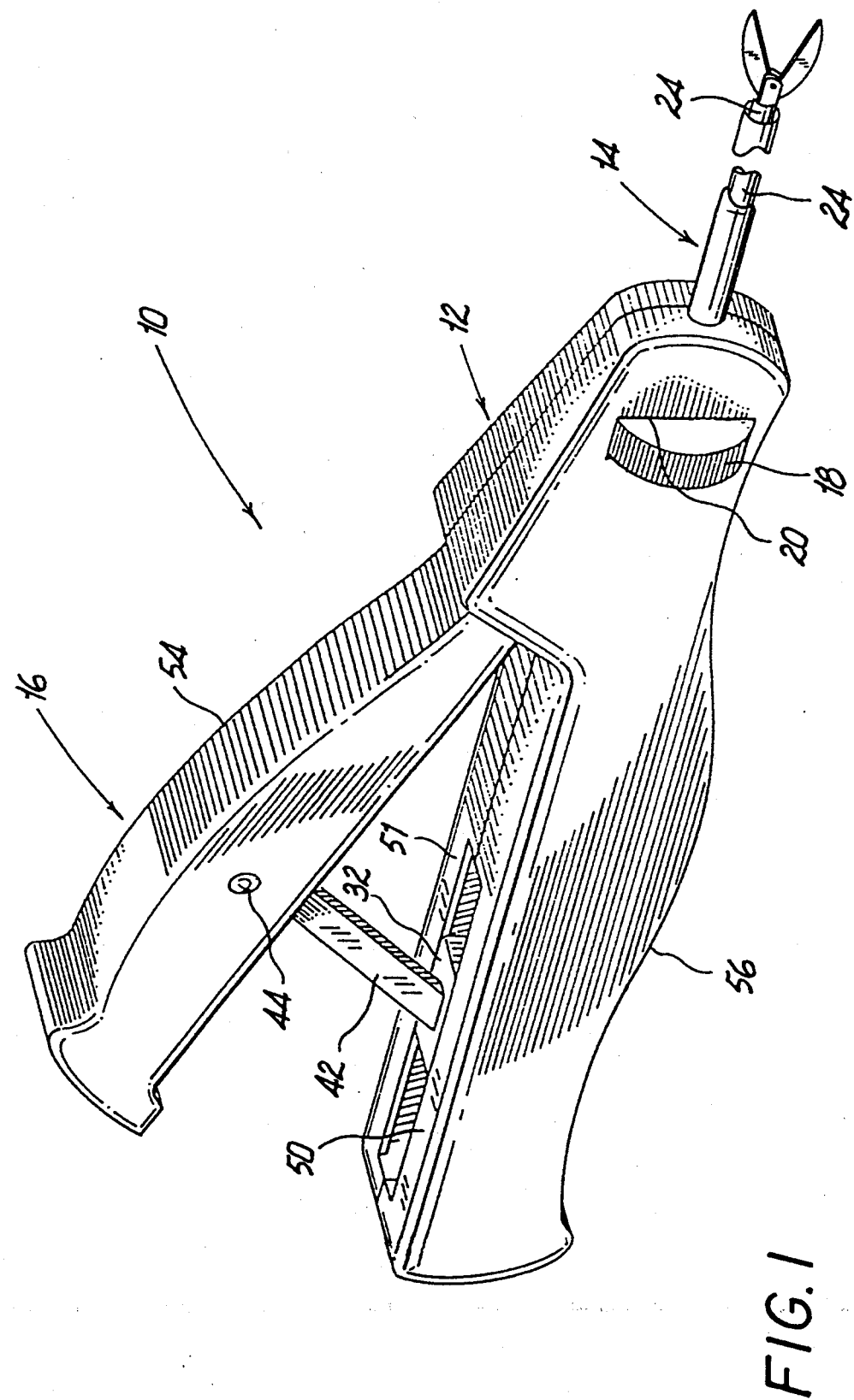
FIG. 1 illustrates a perspective view of a preferred embodiment of the handle for laparoscopic instrumentation according to the present invention.

Referring to FIG. 1, a preferred embodiment of the handle, shown generally as 10, is shown. An elongated casing 12 encloses the essential parts of the invention, which are described in detail hereafter. Handle 10 is suitable for manipulating a distal laparoscopic or endoscopic surgical tool, not shown in the figures, which is attached to the opposite, distal end of a pair of concentric longitudinal shafts 14. Longitudinal shafts 14 extend outwardly from casing 12, and allow the distal laparoscopic surgical tool to be inserted through a small incision in the body and positioned within the body adjacent the organ which is to be excised or repaired, thus allowing surgical procedures to be performed thereon without the need of severe incisions in adjacent body tissues. As discussed in detail hereafter, concentric shafts 14 may comprise a longitudinally movable inner actuating shaft and an outer shaft, which allow the surgeon to control different types of endoscopic tools requiring reciprocal or rotational manipulations. Although it is preferred that concentric shafts 14 may comprise a longitudinally movable inner shaft and an outer shaft, it is within the scope of the invention that the outer shaft be longitudinally movable over the inner shaft.

An elongated grip member 16 is pivotally connected to casing 12. Elongated casing 12 is aligned axially with concentric shafts 14 for purposes as discussed hereafter. By squeezing grip member 16 inward as described in detail hereafter, longitudinal motion may be transferred to the inner shaft. A thumb wheel 18 may be rotated selectively by the surgeon to impart rotary motion to the outer shaft, so that shafts 14 may be rotated about their longitudinal axis. As shown in FIG. 1, thumb wheel 18, may be carried within a pair of opposed slots 20 on opposite sides of casing 12.

Figure 2:
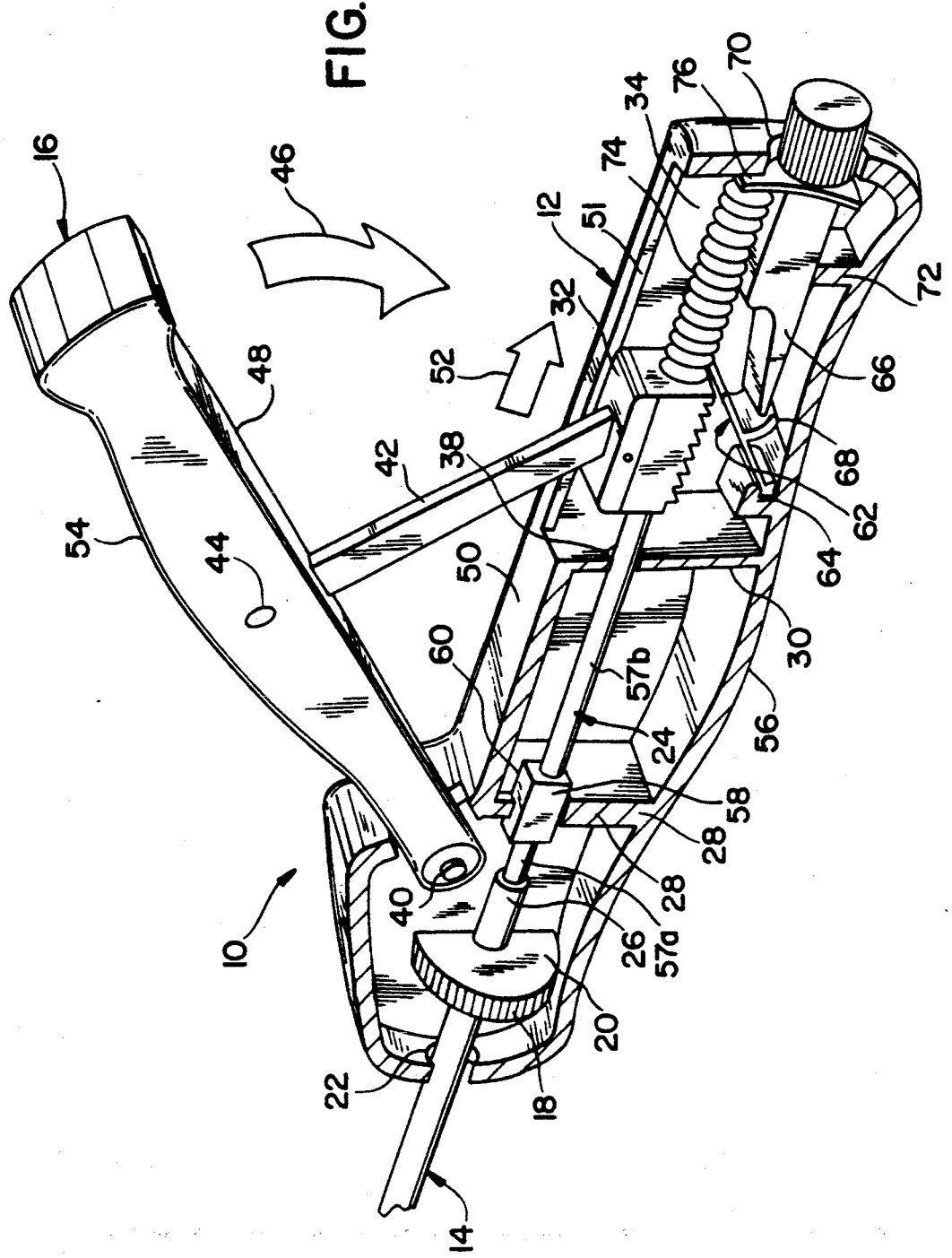
FIG. 2 illustrates a cut-away perspective view of the handle of FIG. 1.

Referring to FIG. 2 for details enclosed by casing 12, concentric shafts 14 extend longitudinally into casing 12 through an opening 22 in the front end of casing 12. Concentric shafts 14 include an inner longitudinal actuating shaft 24 and an outer longitudinal tubular shaft 26, concentrically positioned around inner shaft 24. Actuating shaft 24 extends longitudinally into casing 12 through a pair of opposed openings in inner walls 28, 30. Included with actuating shaft is a rack 32 located in the rearward chamber 34 of casing 12 behind wall 30. Actuating shaft 24 connects at its inner end to rack 32 by any suitable means so that actuating shaft 24 may be moved longitudinally by rack 32, as well as rotatably, if desired. Rack 32 is positioned so that its teeth 36 extend longitudinally along the axis of actuating shaft 24. Opening 38 in wall 30 through which actuating shaft 24 longitudinally extends may provide a bearing surface on which actuating shaft 24 may slide longitudinally, while restraining lateral motion of actuating shaft 24 and rack 32. Attachable at the opposite, distal ends of shafts 24, 26 is a laparoscopic surgical tool, not shown in the figures, which may be manipulated by selective longitudinal and rotative motions of shafts 24, 26 to perform selected surgical procedures.

Figure 3:
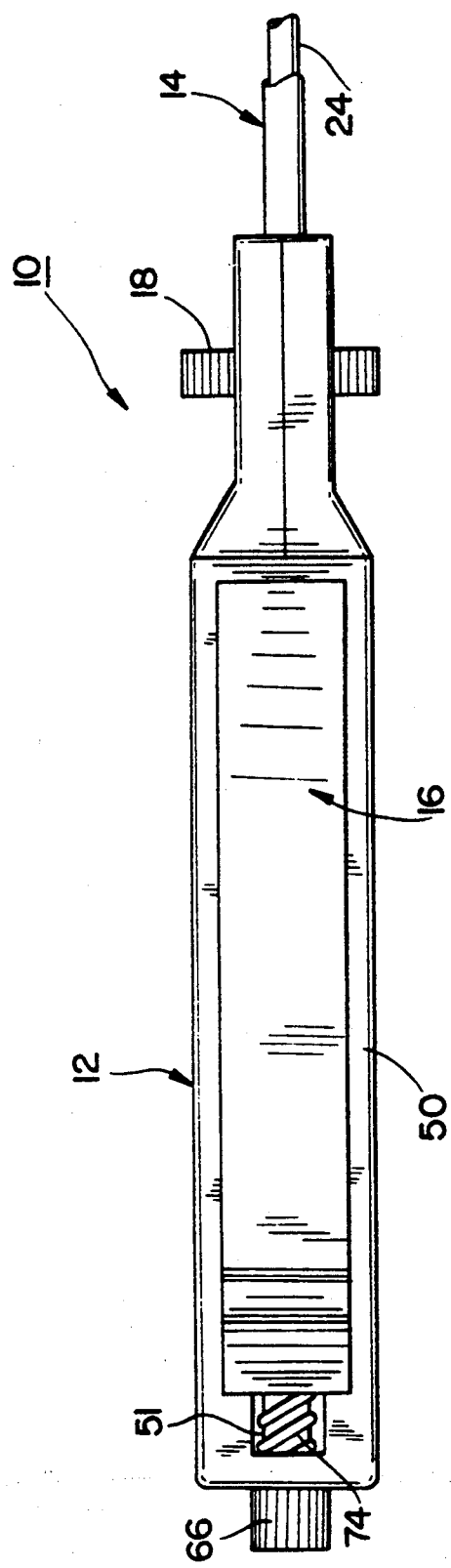
FIG. 3 illustrates a top view of the handle of FIG. 1.

As shown in FIG. 2, elongated grip member 16 is pivotally connected at one end to casing 12 by suitable means such as a pivot pin 40. Elongated casing 12 is aligned axially with concentric shafts 14, and grip member 16 extends generally axially along casing 12, as shown in FIG. 3, from its pivotal connection with casing 12 toward the rear of casing 12. Referring again to FIG. 2, grip member 16 and casing 12 together provide a pair of operating handles movable toward and away from each other. Consequently, a handle is provided which is aligned axially with the axis of the concentric shafts 14. Thus, the user may apply squeezing motion about the common axis of shafts 14. It is known to provide squeezable operating handles that are configured perpendicular to the axis of the concentric shafts. However, at times this handle configuration is difficult for the user to manipulate, which may lead to unpreferred delays in performing the necessary surgical procedure. However, as provided by the present invention, the ability to move grip member 16 and casing 12 toward and away from each other about the common axis of shafts 14 alleviates this problem and allows the user to more easily manipulate the surgical tool under more varied operating conditions. Thus, surgical procedures may be more timely and safely performed.

A link member 42 extends between grip member 16 and rack 32 and is pivotably connected to both at a pivot point. One end of link member 42 is pivotally connected on grip member 16 a suitable distance from its pivotal connection with casing 12 by suitable means such as a pivot pin 44, and the opposite end of link member 42 is similarly attached to rack 32. Grip member 16 is pivotally movable laterally relative to casing 12 from a first position as shown in FIG. 2 inward in the direction of arrow 46 to a second position, not shown in the figures, co-axial with shafts 14, in which a planar surface 48 extending longitudinally along the lower surface of grip member 16 contacts longitudinally along a similar planar surface 50 extending along casing 12. A longitudinal slot 51 in casing 12 allows link member 42 and rack 32 to move longitudinally in casing 12, and may include a cooperating flange and bevel system to provide a track in casing 12 in which rack 32 travels.

As grip member 16 is moved laterally inward toward its second position about its pivotal connection with casing 12, link member 44 translates the pivotal motion of grip member 16 to longitudinal motion to move rack 32 longitudinally in a first direction as indicated by arrow 52 toward the end of casing 12. Movement of rack 32 longitudinally by the inward movement of grip member 16 toward its second position causes actuating shaft 24, connected thereto for movement therewith, to move longitudinally in the same direction as indicated by arrow 52. Movement of actuating shaft 24 longitudinally allows the laparoscopic surgical tool attached at the distal ends of shafts 24, 26 to be manipulated by the longitudinal motion of actuating shaft 24 to provide a specified surgical procedure.

Extending along the upper surface of grip member 16 is an arcuate convex section 54. Located opposite arcuate convex section and extending along the bottom surface of casing 12 is a similar symmetrical arcuate convex section 56. Opposed arcuate convex sections 54, 56 are provided so that handle 10 may be more easily held and manipulated by the user to move the operating handles toward and away from each other, and it is apparent that these curved surfaces may be varied in length and height to provide for an anatomically comfortable grip.

Referring to FIG. 2, actuating shaft 24 may include a pair of axially aligned longitudinal shaft portions 57a, 57b. A connector in the form of a block 58, located between shaft portions 57a, 57b, may rotatively interconnect shaft portions 57a, 57b. Block 58 may rotatively connect with shaft portions 57a, 57b by any suitable means so that shaft portion 57a may rotate about its longitudinal axis. Block 58 is adapted to slide longitudinally within a notch 60 in wall 28. Preferably, notch 60 has a complementary shape to block 58. As shown in FIG. 2, block 58 may have a square cross section, although other suitable cross sections such as triangular are also within the scope of the invention. As shown in FIG. 2, notch 60 has a complimentary square shape, but may have other suitable complementary cross sections to complement other cross sections of block 58 such as a triangular cross section. Block 58 is further provided with a suitable longitudinal dimension such that block 58 remains positioned in notch 60 during the longitudinal movements of shaft 24. Alternatively, block 58 may be eliminated and shaft 24 may be rotatively connected directly to rack 32, such that a notch or circumferential groove is provided to allow for rotation of the shaft 24 while maintaining axial movement. Block 58 may further be adapted to releasably connect with shaft portion 57a so that shafts 14 may be disconnected from casing 12.

A detent provided in the form of a leaf spring 62 allows for the longitudinal movement of activating shaft 24 and rack 32 in the first direction while restraining the longitudinal movement of activating shaft 24 and rack 32 in a second, opposite direction toward the front end of casing 12. Leaf spring 62 may be fixedly attached at its lower end within a lateral slot 64 in casing 12. Leaf spring 62 extends angularly from slot 64 upwards and toward the rear of casing 12, with its upper end beating against rack 32. The angular extension of leaf spring 62 rearwardly allows teeth 36 of rack 32 to slide rearwardly in the first direction across the upper, contacting end of leaf spring 62.

To restrain longitudinal movement of activating shaft 24 and rack 32 in the second or opposite direction, the upper end of leaf spring 62 biases against rack 32 and engages with the teeth 36 of rack 32 to prevent longitudinal movement of shaft 24 and rack 32 toward the front of casing 12. Leaf spring 62 and rack 32 cooperate to allow for incremental "ratcheting action" which allows the laparoscopic surgical tool to be selectively incrementally manipulated by squeezing grip member 16 inward in suitable increments towards its second position. Accordingly, the surgical tool may go through a series of incremental positions as the tool is manipulated by the longitudinal motion of activating shaft 24. It is also contemplated that the pitch and spacing of the teeth 36 may be varied along the length of rack 32 to provide for fine or coarse adjustment during opening and closing. The rearward end of the rack 32 may have teeth having greater spacing between them to allow for coarse adjustment, while the teeth at the forward end may be closely spaced to provide for fine adjustment.

To return the laparoscopic surgical tool to its initial position, handle 10 is provided with a release means for releasing leaf spring 62 from its engagement with rack 32 to allow longitudinal movement of the actuating shaft 24 in the second direction. In a preferred embodiment, the release means is provided by an elongated release member or push button 66 and a catch 68 on leaf spring 62, which when engaged by the end of elongated member 66 when it is moved longitudinally to its second position as described hereafter, causes the upper end of leaf spring 62 to be forced downwardly, thus disengaging leaf spring 62 from teeth 36 of rack 32 and allowing rack 32 and actuating shaft 24 to move longitudinally in the second direction toward the front of casing 12. As may further be appreciated, the release means also allows grip member 16 and link member 42 to return to their first position when release member 66 is moved to its second position.

Release member 66 extends longitudinally through an opening 70 in the rear end of casing 12, where its exposed push button end may be manipulated by pushing to move release member 66 longitudinally. Release member 66 is positioned longitudinally within casing 12 so that its enclosed end may engage catch 68 when release member 66 is moved to its second position. A ledge 72 extends sideways across rearward chamber 34 of casing 12 and prevents release member 66 from moving laterally.

To normally restrain rack 32 and actuating shaft 24 from moving longitudinally in the second direction, biasing means in the form of a compression spring 74 is included with the illustrative release means. Spring 74 retains release member 66 in a first locking position, with its enclosed end disengaged from catch 68. Surrounding release member 66 near its exterior end is a shoulder 76. Spring 74 is located between rack 32 and shoulder 76, and acts against shoulder 76 to normally retain release member 66 locked in its first position, with its enclosed end disengaged from catch 68 as shown in FIG. 2. Spring 74 may be a constant force spring, or may also be a variable force spring in order to allow for easy movement at the beginning of the handle stroke and a harder movement at he end of the stroke to protect the tool mechanism at the end of the shafts.

When release member 66 is moved longitudinally inward toward the front of casing 12 to the second position by finger action pushing on the external portion of release member 66, the enclosed end of release member 66 engages with catch 68 to force the upper end of leaf spring 62 downwardly, thus disengaging leaf spring 62 from the teeth 36 of rack 32 and allowing rack 32 and actuating shaft 24 to move longitudinally in the second direction toward the front of casing 12.

Longitudinal movement of actuating shaft 24 and rack 32 in the second direction toward the front of casing 12 may also be provided by the influence of spring 74. Referring to FIG. 2 for details, spring 74 is compressed longitudinally between rack 32 and shoulder 76. When leaf spring 62 is disengaged from teeth 36 of rack 32 by the movement of release member 66 to its second position, spring 74 biases against the rearward face of rack 32, causing rack 32 and actuating shaft 24 to move longitudinally in the second direction toward the front of casing 12. Movement of actuating shaft 24 longitudinally in the second direction allows the laparoscopic surgical tool attached at the distal ends of shafts 24, 26 to be returned by the longitudinal motion of actuating shaft 24 to their initial configuration.

In a preferred embodiment, concentric shafts 14 may be interconnected so that shafts 14 rotate together about their longitudinal axis. To allow concentric shafts 14 to rotate together, thumb wheel 18 may engage shaft 26 so that rotation of thumb wheel 18 causes shafts 14 to rotate. In a preferred embodiment, thumb wheel 18 may extend radially from shaft 26, and is suitably affixed thereto so that rotation of thumb wheel 18 causes shafts 14 to rotate to allow the laparoscopic surgical tool attached at the distal ends of shafts 24, 26 to be further manipulated in both clockwise and counter-clockwise directions to provide a further specified surgical procedure. One preferred further manipulation is to apply the rotational movement to rotate the laparoscopic tool in an arc about the longitudinal axis of concentric shafts 14. Consequently, the tool may not need to be withdraw and repositioned in the body to access that bodily organ to be excised or repaired, even though the tool may be initially deflected from its designated plane of operation. Instead, rotation of thumb wheel 18 may allow the tool to be repositioned within the desired operating plane.

In operation, a trocar is partially inserted into the body, and the distal laparoscopic surgical tool attached at the end of shafts 14 of handle 10 may be inserted through the cannula of the trocar and positioned laparoscopically adjacent the organ to be excised or repaired. With the aid of a laparoscope, not shown in the figures, the surgeon can manipulate the distal laparoscopic surgical tool by squeezing grip member 16 laterally inward toward casing 12 about the axis of longitudinal shafts 14 to apply longitudinal motion to the laparoscopic surgical tool to manipulate the tool to perform a specific surgical procedure. Manipulation of the laparoscopic surgical tool to best position the laparoscopic surgical tool in the plane of operation may be performed by rotating thumb wheel 18 in clockwise or counter-clockwise directions. Pressing inward on push button 66 to disengage leaf spring 62 from rack 32, causes the laparoscopic surgical tool to return towards an initial configuration under the influence of spring 74. In addition, it is contemplated that release member 66 may be manipulated to disable leaf spring 62 to allow for free opening and closing of grip member 16 in relationship to casing 12.

While the invention has been particularly shown and described with reference to a preferred embodiment, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. A handle for laparoscopic instruments, comprising:
   actually shaft means concentrically positioned and interconnected within outer shaft means;
   elongated casing means having a longitudinal axis and cooperating with said outer shaft means and said actuating shaft means, said outer shaft means and said actuating shaft means extending outward from said casing means generally along said longitudinal axis and said actuating shaft means being longitudinally movable in increments for manipulating a laparoscopic tool attachable at the end of said outer shaft means and said actuating shaft means opposite said casing means;
   means connected to said outer shaft means for imparting selective rotational movement to said actuating shaft means and said outer shaft means with respect to said longitudinal axis of said casing means;
   gripping means pivotally attached to said easing means, said gripping means and said casing means providing a pair of operating handles movable between a first position wherein said gripping means extends at an angle to said longitudinal axis and a second position wherein said gripping means is in substantial parallel alignment with said longitudinal axis, said actuating shaft means being longitudinally movable in a first direction by pivotal motion of said gripping means; and
   detent means carried by said casing means for allowing the movement of said actuating shaft means longitudinally in said first direction while restraining longitudinal movement of said actuating shaft means in a second direction.

2. The handle of claim 1, further comprising link means pivotally interconnecting said gripping means and said actuating shaft means.

3. The handle of claim 2, wherein said gripping means is movable in a laterally pivotable manner from said first position, and said link means translates the lateral pivotable movement of said gripping means to longitudinal motion for longitudinal movement of said actuating shaft means.

4. The handle of claim 1, further comprising rack means movable with said actuating shaft means.

5. The handle of claim 4, wherein said rack means is longitudinally movable along said detent means in said first direction while engaging with said detent means to restrain longitudinal movement of said actuating shaft means in said second direction.

6. The handle of claim 5, further comprising link means pivotally connecting said gripping means and said rack means.

7. The handle of claim 5, wherein said detent means includes a resilient member attached to said casing means.

8. The handle of claim 7, wherein said resilient member is a leaf spring.

9. The handle of claim 7, wherein said rack means includes a rack mounted on said actuating shaft means, said rack having a plurality of teeth disposed consecutively along a longitudinal axis of said actuating shaft means.

10. The handle of claim 9, wherein said rack is longitudinally movable along said resilient member in said first direction while said resilient member connects consecutively along said teeth to restrain longitudinal movement of said actuating shaft means in said second direction.

11. The handle of claim 1, wherein said detent means includes a resilient member that is attached to said casing means.

12. The handle of claim 1, further comprising release means for releasing said detent means to allow longitudinal movement of said actuating shaft means in said second direction.

13. The handle of claim 12, wherein said release means includes biasing means for biasing said release means in a first position to allow longitudinal movement of said actuating shaft means along said first direction.

14. The handle of claim 12, wherein said detent means includes a resilient member.

15. The handle of claim 14, further comprising a rack, said actuating shaft means being connected to said rack for longitudinal movement therewith, said rack being adapted for longitudinal movement along said resilient member in said first direction while engaging with said resilient member to restrain longitudinal movement of said actuating shaft means in said second direction.

16. The handle of claim 15, wherein said release means includes a catch on said resilient member and a release member movable from a first position disengaged from said catch, to a second position to engage said catch and disengage said resilient member from said rack to allow longitudinal movement of said actuating shaft means in said second direction.

17. The handle of claim 16, wherein said release means includes biasing means for biasing said release member in said first position.

18. The handle of claim 17, wherein said biasing means includes a spring.

19. The handle of claim 18, wherein said spring urges against said release member to bias said release member in said first position.

20. The handle of claim 18, wherein said spring is located longitudinally along the axis of said actuating shaft means between said rack and a shoulder extending laterally from said release member, said spring urging said shoulder against said casing to bias said release member in said first position.

21. The handle of claim 16, further comprising biasing means for causing said actuating shaft means to move longitudinally in said second direction when said release member is in said second position.

22. The handle of claim 21, wherein said biasing means includes a spring.

23. The handle of claim 22, wherein said spring is located longitudinally along the axis of said actuating shaft means, said spring causing said actuating shaft means to move longitudinally in said second direction when said release member is in said second position.

24. The handle of claim 23, wherein said spring is located between said rack and a shoulder extending laterally from said release member.

25. The handle of claim 16, wherein said release member is movable will respect to said longitudinal axis of said casing means.

26. The handle of claim 15, wherein said handle further comprises a link member pivotally connecting said gripping means and said actuating shaft means.

27. The handle of claim 26, wherein said gripping means is laterally pivotable from a first position toward said casing means, and wherein said link member translates the lateral movement of said gripping means to longitudinal motion for longitudinal movement of said actuating shaft means.

28. The handle of claim 27, wherein said rack is attached on said shaft means so that said actuating shaft means moves longitudinally with said rack, and wherein said link member pivotally connects said gripping means and said rack.

29. The handle of claim 1, wherein said means for imparting selective rotational movement comprises thumb wheel means connected to said outer shaft means for rotating said outer shaft means and said actuating shaft means.

30. The handle of claim 1, wherein said second direction is an opposite direction.

31. A handle, comprising:
a pair of concentric shafts, said concentric shafts including an inner longitudinally movable actuating shaft and an outer shaft;
an elongated casing having a longitudinal axis and cooperating with said concentric shafts, said concentric shafts extending outwardly from said casing generally along said longitudinal axis, and means secured to at least one of said shafts for imparting rotational movement thereto with respect to said longitudinal axis of said casing to permit manipulation of a laparoscopic tool attachable at a distal end portion of said concentric shafts opposite said casing;
an elongated grip member pivotally attached to said casing, said grip member and said casing providing a pair of operating handles movable between a first position wherein said grip member extends generally at an angle to said longitudinal axis and a second position wherein said grip member is in substantial parallel alignment with said longitudinal axis;
a rack longitudinally movable in said casing, said rack being longitudinally movable in a first direction by pivotal movement of said grip member from said first position to said second position, said actuating shaft being attached to said rack to facilitate incremental longitudinal movement of said actuating shaft within said outer shaft so as to permit further manipulation of the laparoscopic tool in response to said longitudinal movement of said rack; and
a detent carried by said casing, said detent allowing said incremental longitudinal movement of said actuating shaft in said first direction while engaging with said rack releasably restrain longitudinal movement of said actuating shaft in a second direction.

32. The handle of claim 31, further comprising a link member pivotally interconnecting said grip member and said rack.

33. The handle of claim 31, wherein said detent includes a resilient member fixedly attached in said casing.

34. The handle of claim 31, wherein said means for imparting rotational movement comprises a thumb wheel engaged with said outer shaft to transfer rotational motion thereto and rotate said outer shaft.

35. The handle of claim 31, further comprising an elongated release member carried by said casing and longitudinally movable therein, said release member being longitudinally movable with respect to said longitudinal axis of said elongated casing, from a first position to a second position to engage a catch on said detent, and disengage said detent from said rack to allow said actuating shaft to move longitudinally in said second direction.

36. The handle of claim 35, further comprising biasing means carried by said casing for urging said actuating shaft in said second direction when said release member is in said second position.

37. The handle of claim 36, wherein said biasing means includes a spring between said rack and said casing.

38. The handle of claim 35, further comprising biasing means carried by said casing for retaining said release member in said first position.

39. The handle according to claim 31, wherein said means for imparting rotational movement is secured to said outer shaft.

40. A handle, comprising:
a pair of concentric shafts, said concentric shafts including an inner longitudinally movable actuating shaft and an outer shaft having a longitudinal axis
an elongated casing having a longitudinal axis aligned with said concentric shafts, said concentric shafts extending outwardly from said casing generally along said longitudinal axis of said casing, and means for rotating said other shaft about said longitudinal axis of said casing to permit manipulation of a laparoscopic tool attachable at a distal end portion of said concentric shafts opposite said casing;
an elongated grip member pivotally attached to said casing, said grip member and said casing providing a pair of operating handles movable between a first position corresponding to said grip member extending generally at an angle to said longitudinal axis of said casing to a position wherein said grip member is in substantial parallel alignment with said longitudinal axis of said casing;
a rack longitudinally movable in said casing;
a link member pivotally interconnecting said grip member and said rack, said rack being longitudinally movable in a first direction by pivotally moving said grip member from said first position to said second position, said link member translating said pivotal movement of said grip member to incremental longitudinal motion of said rack, and said actuating shaft being attached to said rack to facilitate incremental longitudinal movement of said actuating shaft within said outer shaft so as to permit further manipulation of the laparoscopic tool in response to said incremental longitudinal motion of said rack;

a detent carried by said casing, said detent allowing the longitudinal movement of said actuating shaft in said first direction while engaging with said rack to restrain longitudinal movement of said actuating shaft in a second direction; and a release member carried by said casing and longitudinally movable therein, said release member being movable along to said longitudinal axis of said casing, from first position to a second position to disengage said detent from said rack to allow said actuating shaft to move longitudinally in said second direction.

41. The handle of claim 40, wherein said detent includes a resilient member fixedly attached in said casing.

42. The handle of claim 40, wherein said rotating means comprises a thumb wheel engaged with said outer shaft to transfer rotational motion thereto and rotate said outer shaft.

43. The handle of claim 40, further comprising biasing means carried by said casing for urging said actuating shaft in said second direction when said release member is in said second position.

44. The handle of claim 43, wherein said biasing means includes a spring between said rack and said casing.

45. The handle of claim 40, further comprising biasing means carded by said casing for retaining said release member in said first position.

46. A handle for laparoscopic instruments, comprising:

elongated casing means having a longitudinal axis and means for mounting elongated shaft means therein, said elongated shaft means being aligned with said casing means along said longitudinal axis;

gripping means pivotally attached to said casing means, said gripping means and said casing means providing a pair of operating handles movable between a first position wherein said gripping means extends generally at an angle to said longitudinal axis and a second position wherein said gripping means is in substantially parallel alignment with said longitudinal axis, said casing means including ratchet means for incrementally adjusting a closing stroke of said gripping means relative to said elongated casing means; and means positioned at least partially within said casing means and secured to said elongated shaft means for imparting rotational movement at least to said elongated shaft means.

47. The handle of claim 46, wherein said ratchet means includes rack means interconnected with said elongated shaft means to transfer longitudinal motion thereto, and detent means carried by said casing means for allowing the movement of said rack means longitudinally in a first direction while restraining longitudinal movement of said rack means in a second opposite direction.

48. The handle of claim 47, wherein said closing stroke of said gripping means is translated to longitudinal motion for longitudinal movement of said rack means in said first direction.

49. The handle of claim 47, further comprising release means for releasing said detent means to allow longitudinal movement of said rack means in said second direction.

50. The handle of claim 49, wherein longitudinal movement of said rack means in said second direction is translated to adjust an opening stroke of said gripping means.

51. A handle for laparoscopic instruments, comprising:

elongated casing means having a longitudinal axis and outer shaft means extending outwardly generally along said longitudinal axis from at least one end portion thereof;

actuating shaft means interconnected with said outer shaft means and positioned at least partially within said outer shaft means and said casing means in general axial alignment therewith and extending outwardly from said at least one end portion thereof, a ratchet mechanism for moving said actuating shaft means in longitudinal increments, said actuating shaft means adapted to be associated with a laparoscopic tool for manipulation thereof;

means connected to said outer shaft means for imparting selective rotational movement to said actuating shaft means and said outer shaft means with respect to said longitudinal axis of said casing means;

gripping means attached to said casing means in a manner such that said gripping means and said casing means are pivotally movable relative to each other between a first angularly disposed position, and a second substantially parallel aligned position wherein said gripping means is substantially parallel to the longitudinal axis, and are adapted to move said actuating shaft means longitudinally in a first direction when at least one of said casing means and gripping means is moved toward the other; and means adapted to allow said incremental longitudinal movement of said actuating shaft means in a first direction and preventing longitudinal movement in the opposite direction.

52. A surgical instrument comprising:

a body assembly;

a handle assembly including an axially directed stationary handle and a movable handle, said movable handle being pivotally connected to said stationary handle and being movable from a first position at an angle to said stationary handle to a second position in substantial parallel alignment with said stationary handle and said body assembly and terminating at an end remote from said handle assembly in a reciprocating movable tool mechanism, said body assembly;

said body assembly comprising a pair of coaxial members attached at one end to said handle assembly, including an inner rod member slidable within an elongated outer tube member in response to movement of said handle assembly, which facilitates interaction of said body assembly with said tool mechanism; and a ratchet mechanism positioned within said stationary handle of said handle assembly for engaging said body assembly to provide slidable movement to said inner rod member within said outer tube member in predetermined increments.

53. A surgical instrument according to claim 52, wherein said ratchet mechanism comprises a pawl member which engages a rack member which cooperates with said inner rod member.

54. A surgical instrument according to claim 53, wherein said movable handle is operably connected to said ratchet mechanism by a link member.

55. A surgical instrument according to claim 52, wherein said ratchet mechanism frictionally engages said inner rod member of said body assembly.

56. A handle for laparoscopic instruments, comprising:
- an outer shaft member;
- an actuating shaft member concentrically positioned and interconnected within said outer shaft member;
- an elongated casing having a longitudinal axis and cooperating with said outer shaft member and said actuating shaft member, said outer shaft member and said actuating shaft member extending outward from said casing along said longitudinal axis, said casing including means for in increments for facilitating manipulation of a laparoscopic tool attachable at the end of said outer shaft member and said actuating shaft member opposite said casing;
- a grip member pivotally attached to said casing, said grip member and said casing providing a pair of operating handles movable between a first position wherein said grip member is in substantial parallel alignment with said longitudinal axis, said actuating shaft member being longitudinally movable in a first direction by pivotal motion of said grip member;
- at least one detent carried by said casing for allowing the incremental movement of said actuating shaft member longitudinally in said first direction while restraining longitudinal movement of said actuating shaft member in a second direction; and
- means connected of said outer shaft member for imparting selective rotational movement to said outer shaft member and said actuating shaft member with respect to said longitudinal axis of said casing so as to permit further manipulation of a laparoscopic tool attachable at the end of said outer shaft member and said actuating shaft member opposite said casing.

* * * * *